US010194862B2

(12) United States Patent
 Chakravarthi et al.

(10) Patent No.: US 10,194,862 B2
(45) Date of Patent: Feb. 5, 2019

(54) SMART WEARABLE DEVICE FOR HEALTH WATCH

(71) Applicant: Sensesemi Technologies Private Limited, Bangalore (IN)

(72) Inventors: Veena S Chakravarthi, Bangalore (IN); Praveen Dodagoudar, Harrison, NJ (US); Vishweshwara Mundkur, Bangalore (IN)

(73) Assignee: Sensesemi Technologies Private Limited, Bangalore (IN)

( * ) Notice: Subject to any disclaimer, the term of this patent is extended or adjusted under 35 U.S.C. 154(b) by 134 days.

(21) Appl. No.: 15/279,543

(22) Filed: Sep. 29, 2016

(65) Prior Publication Data

US 2018/0085058 A1 Mar. 29, 2018

Related U.S. Application Data

(60) Provisional application No. 62/271,322, filed on Dec. 28, 2015.

(51) Int. Cl.
*A61B 5/00* (2006.01)
*A61B 5/01* (2006.01)
(Continued)

(52) U.S. Cl.
CPC ............ *A61B 5/681* (2013.01); *A61B 5/0022* (2013.01); *A61B 5/022* (2013.01); *A61B 5/02438* (2013.01); *A61B 5/0456* (2013.01); *A61B 5/1486* (2013.01); *A61B 5/14532* (2013.01); *A61B 5/14552* (2013.01);
(Continued)

(58) Field of Classification Search
CPC ............ A61B 5/14532; A61B 5/14552; A61B 5/150358; A61B 5/681; A61B 5/742; A61B 5/7475; A61B 5/02–5/0295; A61B 5/0402–5/0472; A61B 5/15–5/157; A61B 5/0205; A61B 5/02125;
(Continued)

(56) References Cited

U.S. PATENT DOCUMENTS

| 6,619,835 | B2 * | 9/2003 | Kita | A44C 5/0015 368/10 |
| 2001/0043514 | A1 * | 11/2001 | Kita | A44C 5/0015 368/281 |

(Continued)

*Primary Examiner* — Gary Jackson
*Assistant Examiner* — Jonathan Kuo

(57) ABSTRACT

A wearable device comprising a display dial configured to display various health parameters, a wristband assisting the device to wear on wrist, an eject-able tray comprising a micro-chip, a first spring coupled to the eject-able tray, at least one latch provided with a second spring to hold the eject-able tray within the device by compressing the first spring, and a health monitoring unit provided with multiple sensors to determine various health parameters, wherein compression of the second spring results in the latch to release the eject-able tray which in turn relaxes the compressed first spring to eject the micro-chip outside the device for collecting blood samples. The microchip comprises at least one micro-needle and an enzyme test strip for collecting and analyzing the blood samples. The health monitoring unit comprises at least three conductive sense pads which are collectively operable to provide electrocardiograph (ECG) information.

10 Claims, 12 Drawing Sheets

(51) Int. Cl.
*A61B 5/15* (2006.01)
*A61B 5/021* (2006.01)
*A61B 5/022* (2006.01)
*A61B 5/024* (2006.01)
*A61B 5/044* (2006.01)
*A61B 5/145* (2006.01)
*G16H 50/30* (2018.01)
*A61B 5/0205* (2006.01)
*A61B 5/0245* (2006.01)
*A61B 5/0456* (2006.01)
*A61B 5/1455* (2006.01)
*A61B 5/1486* (2006.01)
*A61B 5/157* (2006.01)

(52) U.S. Cl.
CPC ........ *A61B 5/157* (2013.01); *A61B 5/150022* (2013.01); *A61B 5/150358* (2013.01); *A61B 5/150412* (2013.01); *A61B 5/150862* (2013.01); *A61B 5/01* (2013.01); *A61B 5/0205* (2013.01); *A61B 5/0245* (2013.01); *A61B 5/02125* (2013.01); *A61B 5/02416* (2013.01); *A61B 5/044* (2013.01); *A61B 5/14517* (2013.01); *A61B 5/4845* (2013.01); *A61B 5/7246* (2013.01); *A61B 5/7475* (2013.01); *A61B 2562/0219* (2013.01); *G16H 50/30* (2018.01)

(58) Field of Classification Search
CPC ... A61B 5/02416; A61B 5/0245; A61B 5/044; G08B 21/00–21/0211; G04G 21/00–21/025
USPC ....... 361/679.01–679.03; 340/539.11–539.13
See application file for complete search history.

(56) References Cited

U.S. PATENT DOCUMENTS

| | | | |
|---|---|---|---|
| 2007/0093786 A1* | 4/2007 | Goldsmith | A61B 5/14532 604/890.1 |
| 2010/0004522 A1* | 1/2010 | Varela | A61B 5/14532 600/347 |
| 2012/0060861 A1* | 3/2012 | Van Cleef | A45D 33/30 132/316 |
| 2015/0366518 A1* | 12/2015 | Sampson | A61B 5/7221 600/301 |
| 2016/0370825 A1* | 12/2016 | Ruffing | G06F 1/1635 |
| 2017/0049352 A1* | 2/2017 | Mirov | A61B 5/04085 |

* cited by examiner

SMART WEARABLE DEVICE FOR HEALTH WATCH

CROSS REFERENCES TO RELATED APPLICATIONS

This application claims priority from U.S. provisional patent application No. 62/271,322 filed on Dec. 28, 2015 which is incorporated herein in its entirety by reference.

BACKGROUND

Technical Field

Embodiments of the present disclosure relate generally to a wearable medical device and more specifically to a system and device for monitoring plurality of health parameters and medication delivery in real time.

Related Art

Increased concern over personal health care management has led to a wide variety of personal health monitoring devices. An individual with a health issue needs to visit periodically a medical advisor for diagnosis or treatment purposes. This helps in monitoring health condition to a certain extent but this is not sufficient to provide accurate treatment without knowing daily activities and health status of the individual's health issue every day. This led to increased usage of health monitoring devices especially, smart wearable devices to monitor day-today activities of an individual with daily health reports.

The existing personal health monitoring devices are able to monitor medical conditions of an individual using plurality of sensors and provide regular activities and health stats at regular intervals of time. These health monitoring devices are further provided with wireless network sensors for communicating with other devices. Few of the health monitoring devices are also providing real time analytical tests for an individual without a need to go medical facilities for performing various diagnostic tests.

However, few conventional health monitoring devices are bulky in size. Other conventional health monitoring devices which are portable in size and wearable devices are typically designed for using with respect to a specific activity of the individual but not for monitoring health parameters. Also the conventional health monitoring wearable devices are complicated to use and are specific to a particular health parameter.

Further, these devices fail in providing prompt medical instructions from a desired medical advisor as soon as a health issue occurs. As, the wireless network sensors in these devices are always connected through the wireless communication network, it may be considered as a serious limitation as the individual using these devices are constantly surrounded with wireless signals all the time. These devices fail to enable historic user data over a period of time automatically and periodically. Existing devices fail to diagnose vital parameters like pH, $pCO_2$, $pO_2$, $Na^+$, $K^+$, $Ca^{++}$, Glu, Hct, Lac through analysis through special add on lab on chip inserted to the wearable. Further, the existing devices fail to calculate $cHCO_3^-$, $cTCO_2$, BE (ecf), BE (b), $cSO_2$ and cHgb from analytics through lab on chip.

Therefore, it is required to integrate mechanisms which are necessary to monitor various health parameters of an individual, diagnose, analyze and calculate data using a portable, light weight, reliable and effective wearable device along with prompt and accurate medical assistance or medication delivery in real time and log data for storing historic data for therapeutic monitoring of health parameters for risk assessment. It is further required to devise a mechanism to communicate the health parameters over long distance of around 10 to 20 Kms range to plurality of machines in a network on a secured link through RF communication consuming very low power.

SUMMARY

According to an aspect of the present disclosure, a wearable device comprising a display dial configured to display various health parameters, a wristband assisting the device to wear on wrist, an eject-able tray comprising a micro-chip, a first spring coupled to the eject-able tray, at least one latch provided with a second spring to hold the eject-able tray within the device by compressing the first spring, and a health monitoring unit provided with multiple sensors to determine various health parameters, wherein compression of the second spring results in the latch to release the eject-able tray which in turn relaxes the compressed first spring to eject the micro-chip outside the device for collecting blood samples. The microchip comprises at least one micro-needle and an enzyme test strip for collecting and analyzing the blood samples. The health monitoring unit comprises at least three conductive sense pads which are collectively operable to provide electrocardiograph (ECG) information. In an embodiment, the wristband comprises an inflatable inner flap coupled to a micro pump and a solenoid facilitating inflation and deflation of the inner flap to determine blood pressure of an individual.

According to another aspect of the present disclosure, the wristband further hosts multiple sensors comprising an accelerometer, a pulse plethysmogram (PPG) sensor, a glucometer, a pressure/force sensor and a temperature sensor that are electrically coupled to the central processing unit. In another embodiment, the PPG sensor and the conductive sense pads are collectively operable to measure systolic and diastolic blood pressure non-invasively by determining a pulse transit time (PTT).

Several aspects are described below, with reference to diagrams. It should be understood that numerous specific details, relationships, and methods are set forth to provide a full understanding of the present disclosure. One who skilled in the relevant art, however, will readily recognize that the present disclosure can be practiced without one or more of the specific details, or with other methods, etc. In other instances, well-known structures or operations are not shown in detail to avoid obscuring the features of the present disclosure.

DETAILED DESCRIPTION OF THE PREFERRED EXAMPLES

Figure 1A:
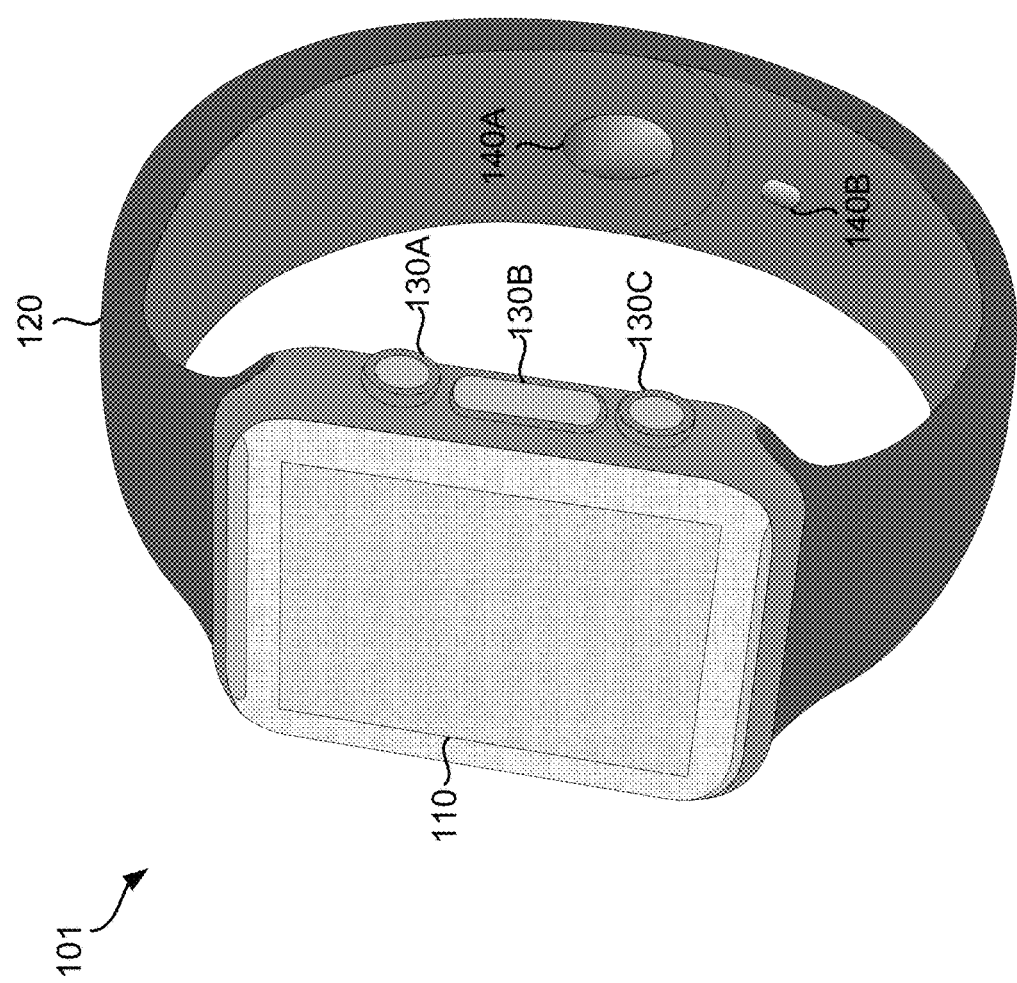
FIG. 1A is a diagram illustrating a smart wearable health monitoring device in an embodiment of the present disclosure.

FIG. 1A is a diagram illustrating a smart wearable health monitoring device in an embodiment of the present disclosure. The smart wearable health monitoring device of the present disclosure may look alike a wrist watch or a bracelet around the wrist of a person's hand which is able to monitor body physiological parameters for example, blood pressure by two methods, blood glucose, heart rate, cardiac activity by means of electrocardiograph (ECG) and body temperature in a user friendly manner. It comprises additional features such as but not limited to time, alarm and alerts for next measurement and the like. The device comprises various units that are electrically interconnected to a central processing unit within the device. In an embodiment, the various units comprise a blood pressure monitoring unit, a blood glucose monitoring unit, ECG unit, body temperature monitor unit and a heart rate monitor unit. All parameters from these units are collected and analyzed by the central processing unit to assess the health of a user and represents health stats on a health scale over a period of time on a display dial.

As shown in the FIG. 1A, the device 101 comprises a central unit (here onwards referred to as a display dial) 110 substantially similar to a wrist watch dial, a flexible wristband 120 coupled to the display dial, plurality of buttons (130A through 130C) for performing various operations and at least one electrode (140A and 140B) coupled within the wristband 120 and/or at bottom of the display dial 110 which in turn electrically connected to the central processing unit within the device 101. All these units are either collectively or independently generates an electric signal corresponding to a chosen health parameter which are processed and displayed on the display dial. The structural and functional aspects of all the units are further discussed in the following figures.

Figure 1B:
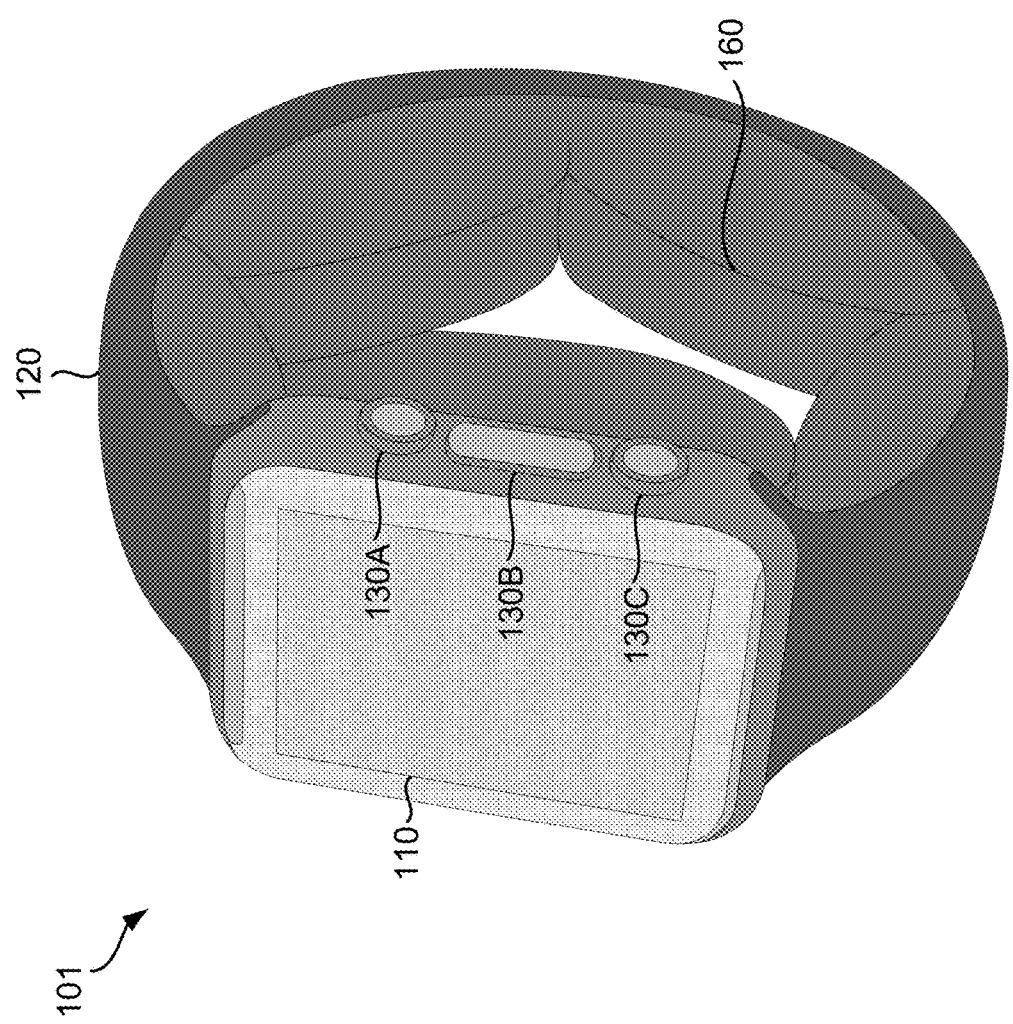
FIG. 1B is a diagram illustrating detection of blood pressure of an individual using the smart wearable health monitoring device in an embodiment of the present disclosure.

FIG. 1B is a diagram illustrating detection of blood pressure of an individual using the smart wearable health monitoring device in an embodiment of the present disclosure. The blood pressure monitoring unit of the smart wearable health monitoring device comprises an inflatable inner flap inside the wristband 120 along with a pressure sensor, a micro pump and a solenoid coupled together within the wristband 120. The flap 160 on the wristband gets inflated with activation of the blood pressure unit which halts blood flow through vein of the user hand wherein the pressure sensor senses the pressure exerted during the inflation and deflation of the flap 160 which helps in determining blood pressure of the user. In an embodiment, the inflation of the flap 160 is achieved by using the micro pump whereas the deflation is attained by using the solenoid. By collapsing and releasing artery under cuff of the user in a controlled manner, blood pressure is determined using the pressure sensor. In another embodiment of the present disclosure, the pressure sensor comprises a micro-electro-mechanical system (MEMs) based piezo resistive pressure sensor with sensitivity of measuring the pressure ranging between 0-25 KPa.

Figure 1C:
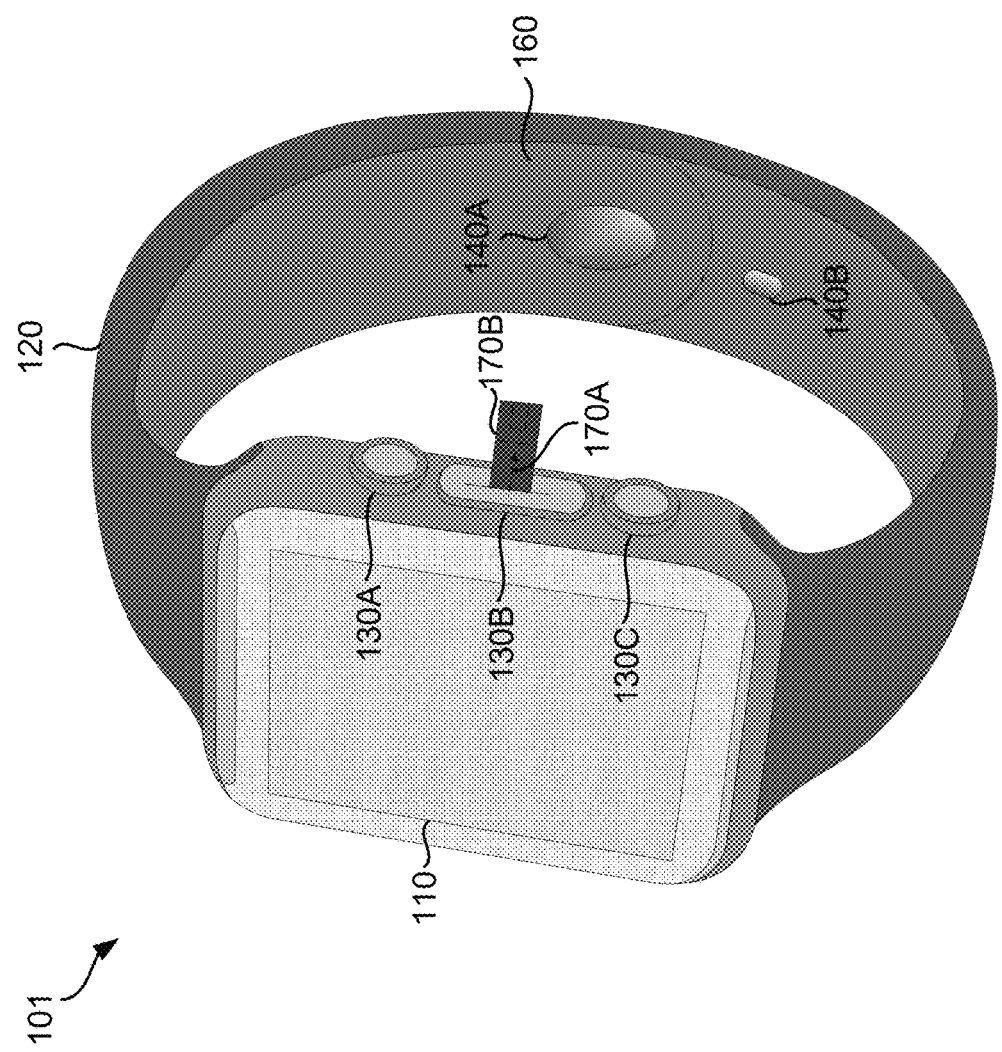
FIG. 1C is a diagram illustrating measurement of blood glucose levels of an individual using the smart wearable health monitoring device in an embodiment of the present disclosure.

FIG. 1C is a diagram illustrating measurement of blood glucose levels of an individual using the smart wearable health monitoring device in an embodiment of the present disclosure. The blood glucose monitoring unit of the device 101 comprises an electronic processing unit, eject able micro-needle 170A and enzyme test strip 170B that are coupled together by a mechanical means. In an embodiment, the micro-needle 170A and the enzyme test strip 170B are coupled together by using a mechanical spring system that helps in ejection mechanism of the micro-needle 170A and the enzyme test strip 170B through the button 130B of the device 101. The micro-needle 170A helps to prick the individual finger to ooze blood sample out which is to be placed on the enzyme test strip 170B. The enzyme present on the test strip 170B triggers an electro-chemical reaction with the blood sample and generates a current that is directly proportional to the levels of blood glucose of the individual. In an embodiment, the micro-needle 170A and the enzyme test strip 170B are replaceable once after usage.

Figure 1D:
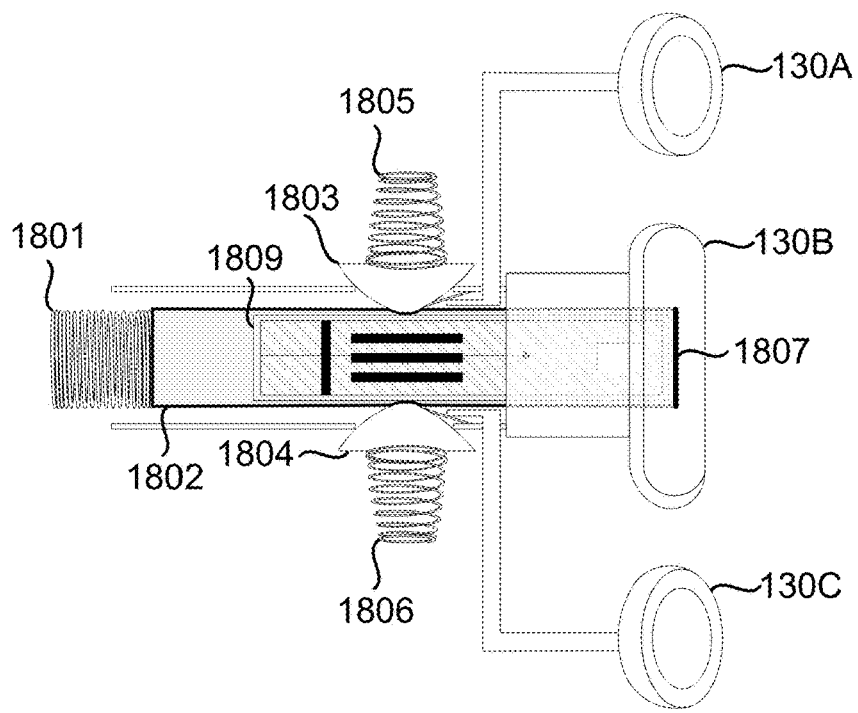
FIG. 1D and FIG. 1E are the block diagrams illustrating the mechanism involved in ejecting the micro-needle and the enzyme test strip for measuring the blood glucose levels in another embodiment of the present disclosure.
Figure 1E:
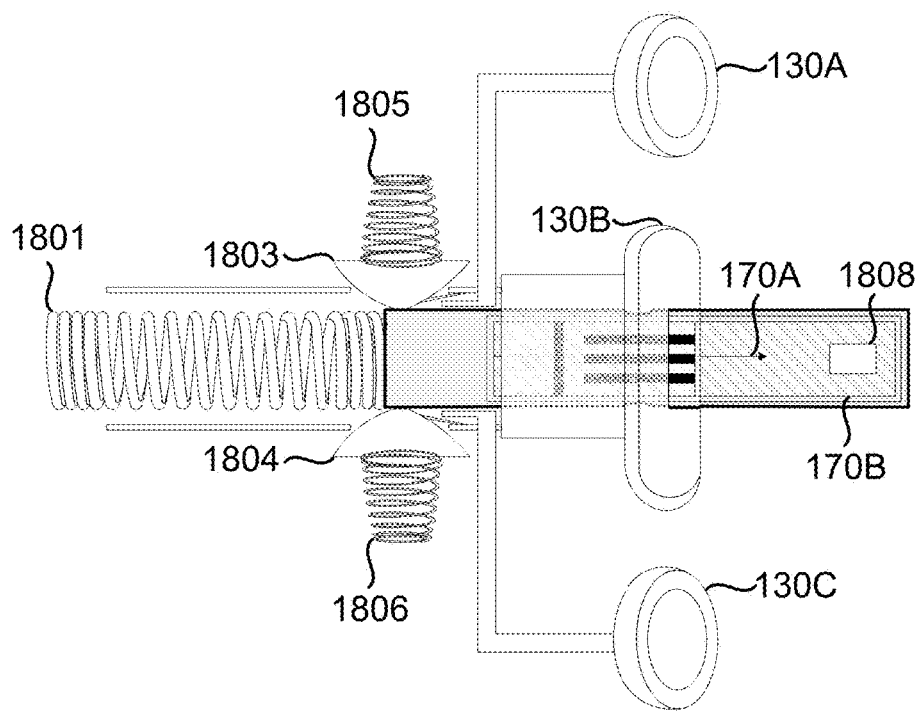

FIG. 1D and FIG. 1E are the block diagrams illustrating the mechanism involved in ejecting the micro-needle and the enzyme test strip for measuring the blood glucose levels in another embodiment of the present disclosure. As shown there, the mechanical spring system involved in ejection of the micro-needle 170A and the enzyme test strip 170B comprises plurality of buttons (130A through 130C), a pair of latches (1803 & 1804) opposite to each other supported by less tension springs (1805 & 1806), a high tension spring 1801, a chamber/tray 1802 and a lab-on-chip (micro-chip) 1809 firmly holding the micro-needle 170A and the enzyme test strip 170B. The button 130B is provided with an aperture for movement of the chamber through the device as desired. In an embodiment, the mechanical spring system is activated by pressing the buttons 130A and 130B at a time to move the latches 1803 and 1804 upwards compressing the less tension springs 1805 and 1806. This result in release of tension stored in the compressed high tension spring 1801 which in turn pushes the tray 1802 outside through an aperture 1807 of the button 130B. Thus, the micro-needle 170A and the enzyme test strip 170B comes out of the device through the aperture 1807 provided on the button 130B.

The micro-needle 170A is then used to prick the individual's finger to get blood sample and then placed the blood sample on a sample marking zone 1808 provided on the enzyme test strip 170B. Then the tray 1802 is then pushed back to its original position through the aperture 1807 which compresses the high tension spring 1801 to its initial position. In an embodiment, the tray 1802 is further provided with a pair of slots on either side which helps in locking the latches 1803 and 1804. Thus latch-lock mechanism is achieved to hold the tray 1802 within the device 101. The enzyme test strip 170B comprises at least two electrodes to determine current generated when the electro-chemical reaction takes place between the enzyme on the strip 170B and the blood sample. This is achieved by using highly sensitive signal processing circuit in the blood glucose monitoring unit and with the advanced processing algorithms, the blood glucose concentration may be provided in milligram per deciliter (mg/dl) with improved measurement period of 2.25 seconds compared to the conventional meters which gives results in 5 seconds. In another embodiment, the lab-on-chip 1809 comprising the micro-needle 170A and the enzyme test strip 170B in the tray 1802 provides additional analysis of blood deriving additional parameters that are required for an expert therapeutic advice. In yet another embodiment, the lab-on-chip 1809 further comprises plurality of the micro-needles 170A and the enzyme test strips 170B wherein each micro-needle and the enzyme test strip are discarded or made non-eject-able after one usage. The lab-on-chip 1809 is further replaceable with an unused chip within the tray 1802 after usage of all the plurality of the micro-needles 170A and the enzyme test strips 170B.

Figure 1F:
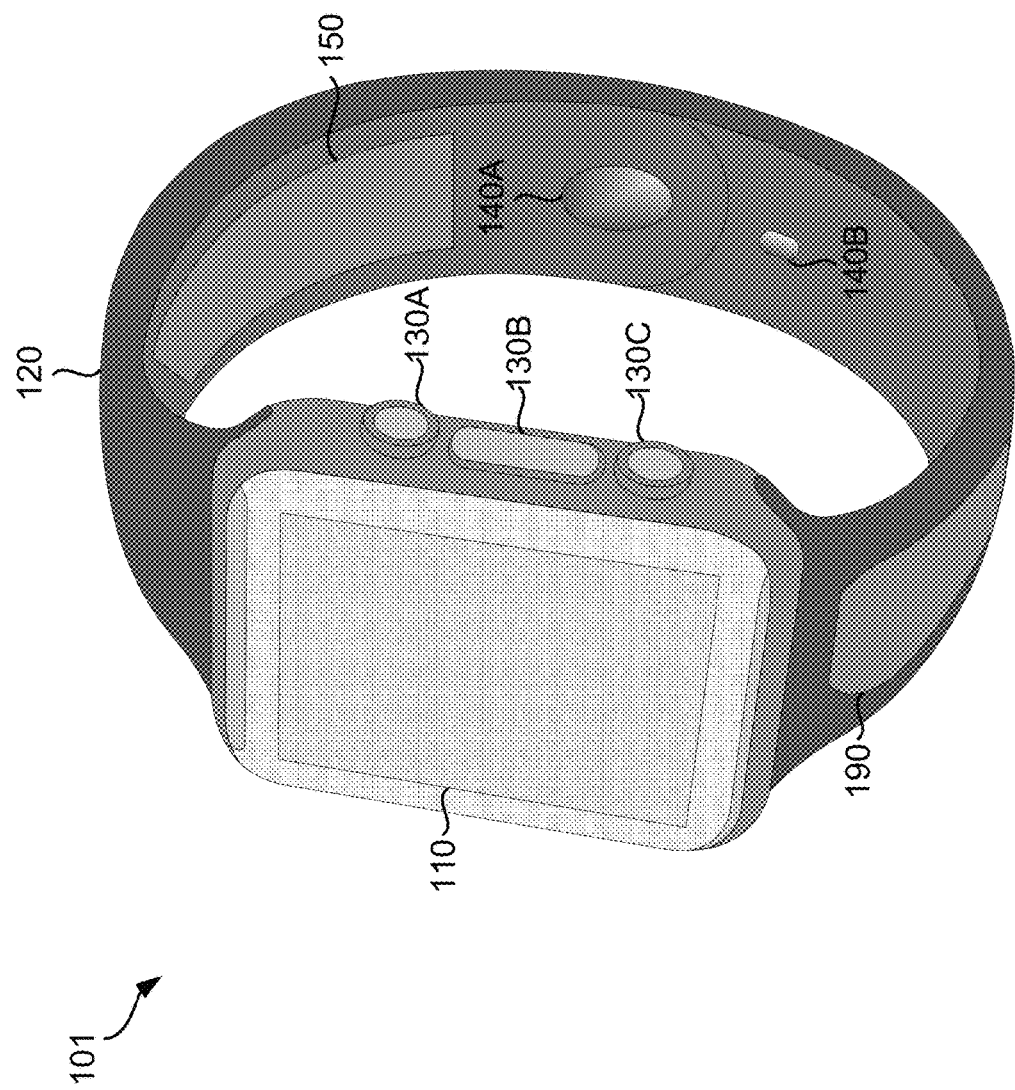
FIG. 1F is a diagram illustrating determination of electrical activity of heart of an individual using the smart wearable health monitoring device in yet another embodiment of the present disclosure.

FIG. 1F is a diagram illustrating determination of electrical activity of heart of an individual using the smart wearable health monitoring device in yet another embodiment of the present disclosure. The electrocardiogram (ECG) is one of the most important tests for diagnosing heart diseases and a widely used tool for monitoring a patient's condition. Conventionally, ECG is obtained by placing plurality of electrodes on opposite sides of the heart of the patient's body to record its electrical activity. The electrodes are transducers that detect minute ionic currents associated with bio-potentials. The electrodes may comprise of silver (Ag) with silver chloride (AgCl) surface or any MEMs conductive material coated on a metallic substrate. For ECG applications at least three electrodes may be required to place on the patient's body for example, one electrode on each arm while a third electrode on right leg. The arm electrodes detect minute differential bio-potentials associated with the heart activity whereas the third electrode provides a common mode drive voltage.

The ECG unit of the smart wearable health monitoring device comprises plurality of embedded sense pads 150 and 190 with a cover in which at least one sense pad 150 at rear side of the display dial 110 or the wristband 120 touching the skin/arm of the patient and other sense pad 190 on top of the wristband 120 facing front side. When a finger of the other hand is placed on the sense pad 190 on top of the wristband 120, the conducting electrodes mounted on the sense pads 150 and 190 captures the ECG signals and processed corresponding to heart activity. In an embodiment, the ECG signals are recorded by using two electrodes along with a reference electrode that filters and removes noise from the obtained signals. These signals detect abnormality in heart functions by comparing with reference healthy benchmark signal that is pre-stored within the device 101. Further, the smart wearable health monitoring device of the present disclosure is provided with a sensitive microphone that is used to record heartbeat of an individual when wrist is held close to chest area of the individual's body.

Figure 1G:
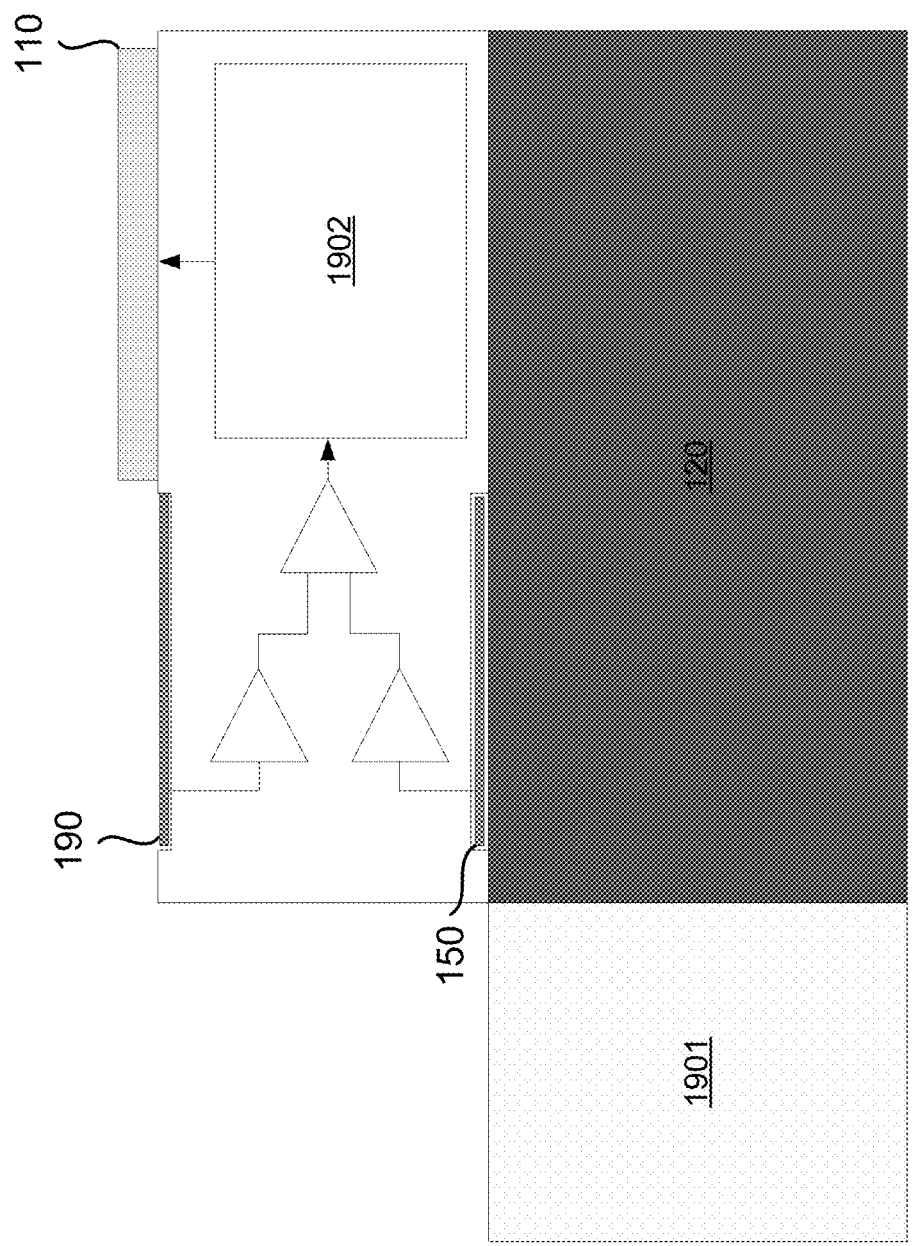
FIG. 1G is a block diagram illustrating the manner in which ECG unit of the device is employed in an embodiment of the present disclosure.

FIG. 1G is a block diagram illustrating the manner in which ECG unit of the device is employed in an embodiment of the present disclosure. As shown there, the ECG unit of the device comprises at least two electrodes of which one electrode (sense pad 150) touching the skin or arm 1901 of the individual under the wristband 120 whereas the other electrode (sense pad 190) on top of the wristband 120 facing front side of the device 101. Once the second electrode (sense pad 190) on front side is touched with finger of another hand, an electric pulse is generated from each of the conductive electrodes (sense pads 150 and 190). These electric pulses are then amplified into an analogue signal which in turn converted into a digital signal by using an analogue to digital converter 1902 within the central processing unit of the device 101. The converted digital signal is then displayed on the display dial 110 of the device 101 as an electrocardiograph representing electrical activity of the heart. In an embodiment, a third electrode may be employed as a reference electrode to reduce or cancel noise generated from the other two electrodes in order to get accurate ECG from the device 101.

Figure 2A:
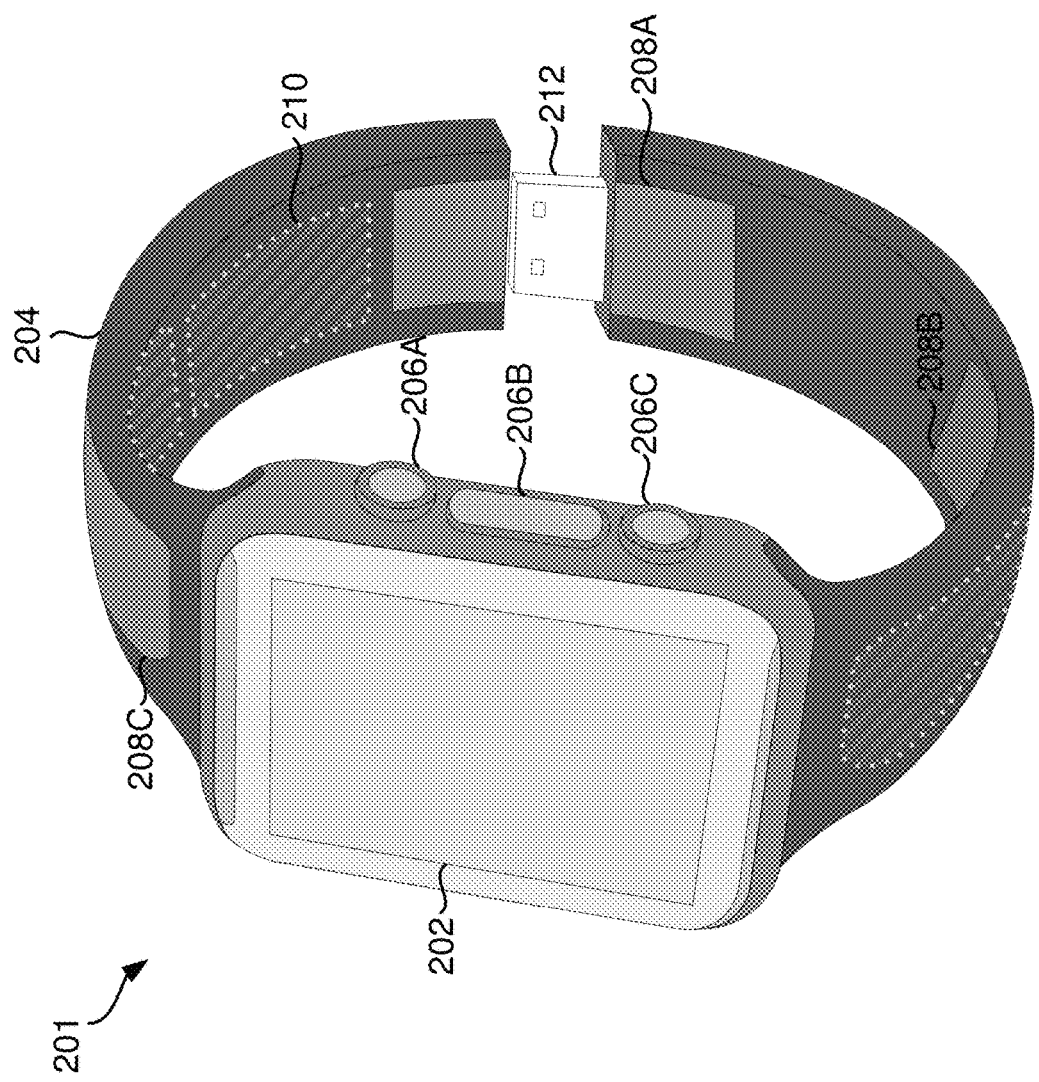
FIG. 2A is a diagram illustrating cuff-less blood pressure measurement by using the smart wearable health monitoring device in another embodiment of the present disclosure.

FIG. 2A is a diagram illustrating cuff-less blood pressure measurement by using the smart wearable health monitoring device in another embodiment of the present disclosure. The smart wearable health monitoring device 201 of the present disclosure comprises an a display dial 202, wristband 204, plurality of buttons (206A through 206C) and at least three sense pads (208A through 208C) that are functional in substantially similar way to that of the sense pads 150 and 190 as discussed in the FIG. 1F. In an embodiment, the plurality of buttons (206A through 206C) helps in activating the spring and latch mechanism, to select a health parameter for display and to configure the central unit. The device 201 further comprises a pulse plethysmogram (PPG) sensor 210 and a USB connector 212 as shown. The USB connector 212 is configured to connect, transfer and/or store data in external devices provided with secured authentication of the user of the device 201. In an embodiment, the USB connector 212 is attached to the flexible wristband and electrically coupled to the central processing unit for external interface such that the USB connector operates as a buckle to the wristband. In another embodiment, the cuff-less blood pressure measurement is achieved by using data obtained from PPG sensor and the ECG signals (from the three sense pads) of the device 201.

The two sense pads 208A and 208B of the device 201 are located on inner side of the wristband 204 that comes in contact with skin of the user's body. When the device 201 is worn on to the left arm, the two sense pads 208A and 208B serve as electrodes placed on left arm and right leg. In addition to these two sense pads, another sense pad 208C is provided on top of the wristband above the display dial 202. This sense pad 208C serves as an electrode placed on right arm which helps in noise cancellation and obtaining accurate ECG signals. In order to get accurate ECG signals, the sense pads 208A and 208B are fastened to the wrist by using the wristband 204 and right hand palm is to be placed on top of the sense pad 208C located above the display dial 202 of the device 201. Then electric pulses from all the three sense pads (208A through 208C) are amplified and converted to a digital signal by the central processing unit of the device 201.

The PPG sensor 210 is used to measure oxygen content in the blood by passing a light source for example, infrared light through a targeted artery and determining absorbed light as a measure of oxygen content in the blood. In an embodiment, the PPG sensor 210 may be coupled with an add-on connector comprising a finger clip or an ear lobe to determine oxygen content in the blood. In another embodiment, the PPG sensor 210 of the smart wearable device comprises an external sense pad mounted on outer surface of the wrist band that functions substantially similar to that of the add-on connector. In an example, information from the PPG sensor 210 is extracted from tip of the right index finger. This is accomplished by wrapping the right palm around the left wrist covering the device 201 wherein tip of the right index finger is in contact with the PPG sensor 210. This also acquires ECG signals from the three sense pads (208A through 208C) that are used for detecting R peak which in turn is used for measuring blood pressure along with the information extracted from the PPG sensor 210.

Figure 2B:
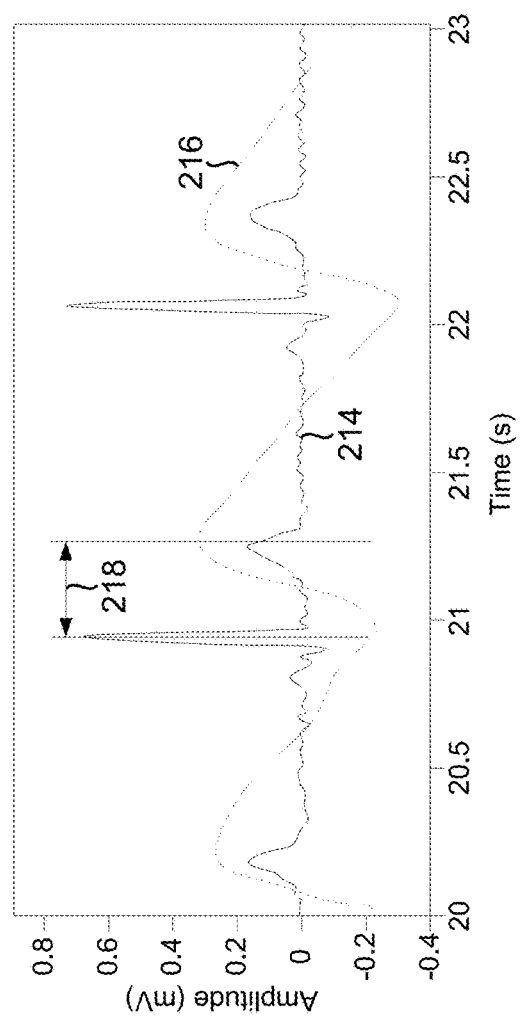
FIG. 2B and FIG. 2C are the diagrams illustrating ECG signal and pulse plethysmogram (PPG) facilitating the cuff-less blood pressure measurement in an embodiment of the present disclosure.
Figure 2C:
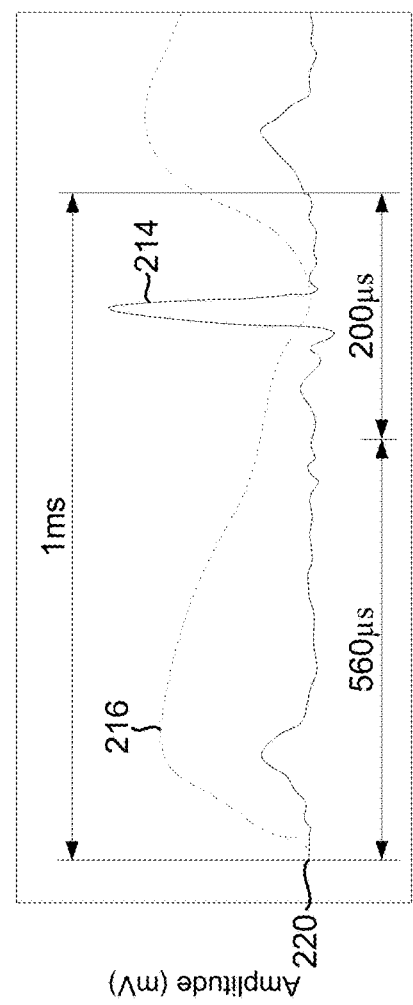

FIG. 2B and FIG. 2C are the diagrams illustrating ECG signal and pulse plethysmogram (PPG) facilitating the cuff-less blood pressure measurement in an embodiment of the present disclosure. In an embodiment, the blood pressure is also derived using cuff-less method from the device 201 of the present disclosure by combined capture of heart rate form the PPG and the ECG signals (214 and 216). The heart rate by the PPG sensor and the ECG signals are time synchronized wherein the blood pressure is derived with single shot signal processing algorithm. In order to measure the blood pressure by cuff-less method, it is required to determine pulse transit time (PTT) 218 from a combined signal of the PPG and the ECG signals (214 and 216). The PTT 218 is the time taken for a pulse to start from heart to a location on body (for example, tip of the right index finger). This is determined as the time difference in peaks of the ECG (R peak) and PPG signals (214 and 216) obtained as shown in the FIG. 2B. The relation between the time taken for a pulse to travel from the heart to a particular location of the body is directly related to the blood pressure which is provided by a generalized equation, $$\text{Blood pressure} = a \times \text{Pulse wave velocity(PWV)} + b$$

where, a and b are constants that are determined by least square algorithm and the PWV is determined from the PTT 218 as a rate at which the pulse propagates through the circulatory system. From the above mentioned correlation, the blood pressure (both systolic and diastolic blood pressure) is thus derived through linear regression approach.

In an embodiment, the PTT (218) is determined by the central processing unit based on algorithm and correlation provided within the processing unit of the device 201. Once the PPG sensor 210 is initialized at 220, the central processing unit of the device 201 extracts PPG information from the PPG sensor 210 and generates a digital signal 216. Similarly, the ECG signal 214 is also generated from the sense pads 208A through 208C which is combined with the PPG signal 216 as shown in the FIG. 2B by the central processing unit. For determining blood pressure through PTT 218, the central processing unit of the device 201 is required to consider a sample from the combined ECG and PPG signal information. In an embodiment, each sample from the combined signal comprises at least one peak of ECG as well as one peak of PPG signal as shown in the FIG. 2C. Further, it is determined that at least one R peak of the ECG signal and one peak of the corresponding PPG signal are obtained within every 1 ms of the combined signal information. In an example, for a sample within time period of 1 ms, the PPG signal 216 peak is obtained between 560 μs from the initialized point 220 whereas the R peak of the ECG signal 214 is obtained between 200 μs after the PPG signal 216 peak. Hence the central processing unit is configured to process the combined signal information of the PPG and ECG signals (214 and 216) within 1 ms for each sample to determine blood pressure by cuff-less method. This ensures that there is no need of time synchronization for using the PPG sensor and the sense pads 208A through 208C to determine the blood pressure using the cuff-less method.

Figure 3A:
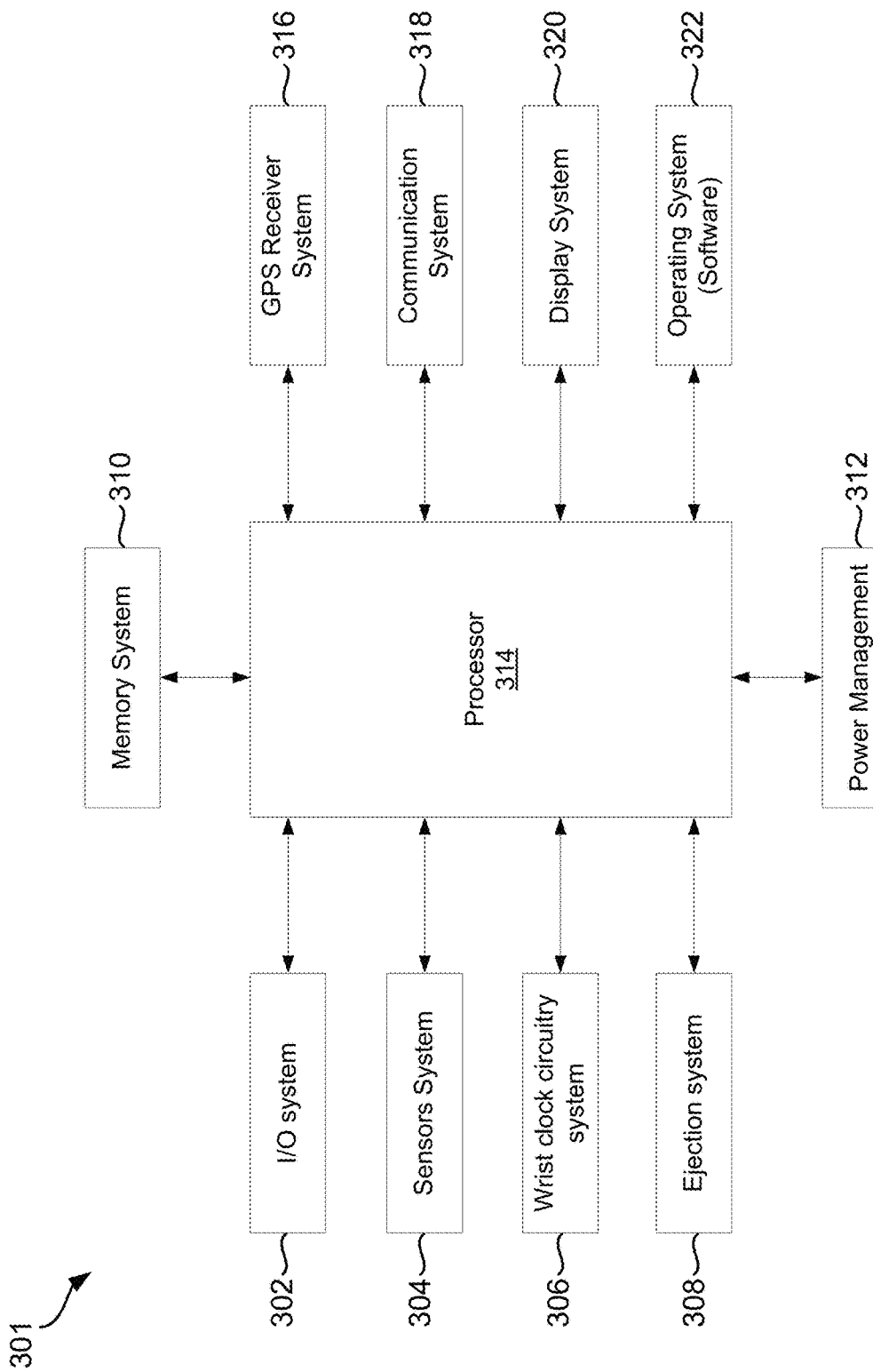
FIGS. 3A and 3B are the internal block diagrams illustrating an example smart wearable health monitoring device in which several aspects of the present disclosure may be deployed.
Figure 3B:
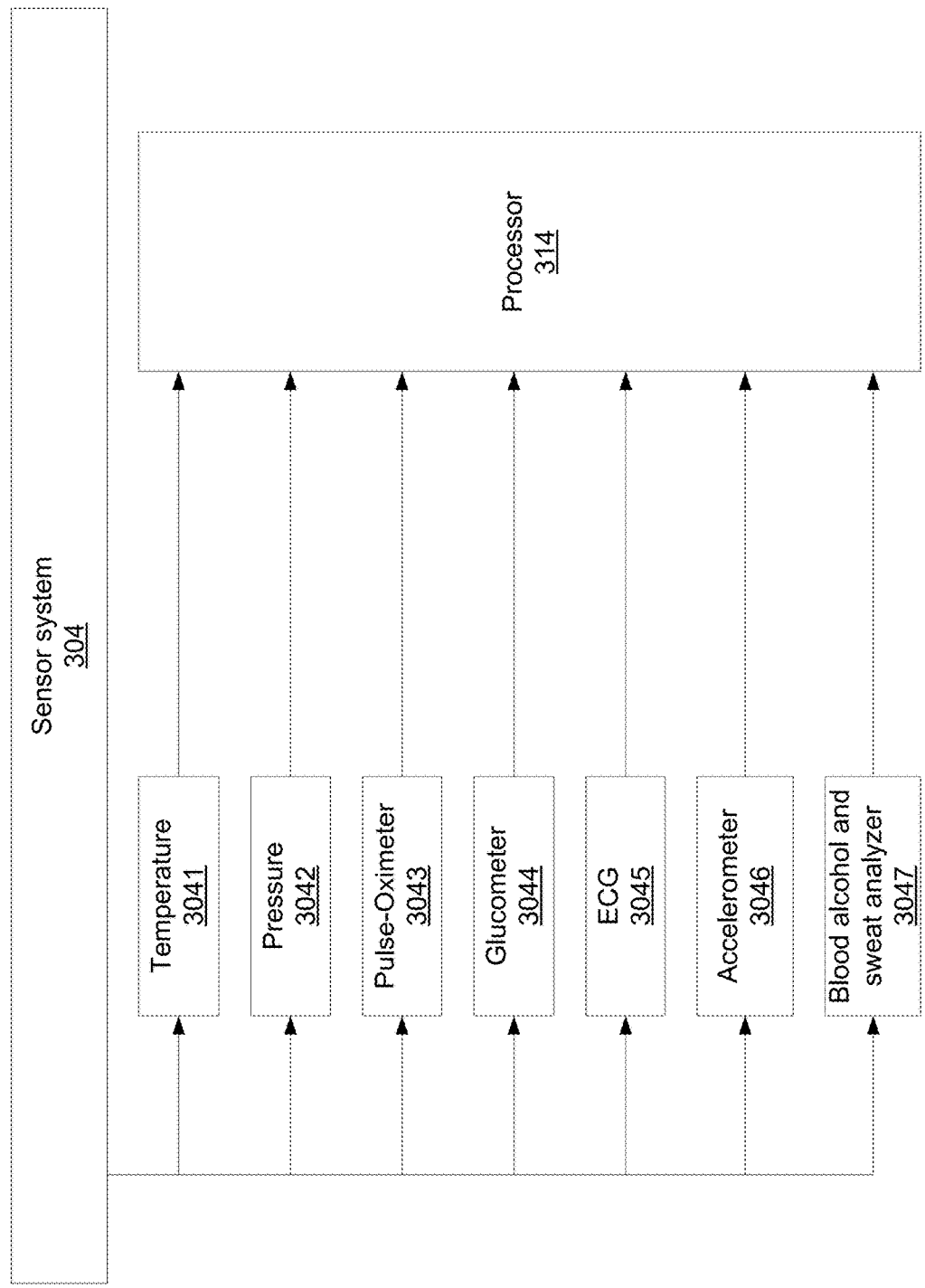

FIGS. 3A and 3B are the internal block diagrams illustrating an example smart wearable health monitoring device in which several aspects of the present disclosure may be deployed. As shown in the FIG. 3A, the example device 301 is shown comprising an input/output (I/O) system 302, a sensor system 304, a wrist clock circuitry system 306, an ejection system 308, a memory system 310, a power management unit 312, a processor 314, a GPS receiver system 316, a communication system 318, a display system 320 and an operating system 322. Each element is described in further detail below.

The I/O system 302 enables an exchange of information, data or commands to and from the device 301 with external systems or a user. The I/O system 302 comprises, but is not limited to, a keyboard/pad, touch screen, USB ports, wireless ports, smart card interface, mouse and/or other control devices. The sensor system 304 is configured to determine the status and conditions around the device 301. The sensor system 304 comprises multiple sensors deployed throughout the device 301 to determine the condition around the device 301 by working in conjunction with one another or independently of one another. In one embodiment, the sensor system 304 is configured to determine the context under which the device 301 is being used. The sensor system 304 includes sensors such as, but is not limited to, sensors for measuring temperature, humidity, motion, torque, magnetic orientation and/or other parameters. In one embodiment, the sensor system 304 includes a pressure sensing piezo-resistive sensor configured to provide blood pressure of an individual from the measured pressure.

The wrist clock circuitry system 306 is configured to display time including hours, minutes, seconds and milliseconds but not limited to alarm, stopwatch settings and the like. The wrist clock circuitry includes an electric stepping motor connected to a microchip through a circuit connection. Further, the wrist clock circuitry comprises but not limited to a crystal oscillator, a crown screw to set time, gears to turn hour, minute and second hands at different speeds. The ejection system 308 is configured to eject a tray out from the device 301 for collecting real time data. The ejection system comprises latches, high tension springs, less tension springs, ejection tray coupled together as discussed in the FIG. 1D and FIG. 1E. The memory system 310 is configured to store data and instructions (e.g., one or more programs) for execution by the processor 314. The memory system 310 provides a direct interface with other system in the device 301 or through the processor 314. The memory system 310 comprises one or more of data memory and program memory. The memory system 310 includes, but is not limited to, different types of Read Only Memory (ROM), Random Access Memory (RAM), external memory disks, removable disks, flash, caches and data cards, for example.

The power management unit 312 provides power to the device 301 to perform desired operation. The power management unit may comprise, for example, batteries, line power or both, circuitry, integrated circuits and other functional modules to manage and distribute power to various components 302 through 322. The processor 314 is configured to execute instructions to perform various mathematical and control operations. The processor 314 comprises one or more processors or processor cores operating in conjunction to execute multiple instructions sequentially or simultaneously. The processor 314 comprises processors or cores customized to efficiently perform specific tasks, such as one or more Digital Signal Processing (DSP) cores, Math coprocessors etc. In one embodiment, the processor 314 is configured to perform operations related to systems 302 through 322 by executing a respective set of instructions (programs) stored in, for example, the memory system 310. Thus, the processor 314 lends processing power to systems 302 through 322 and operates as part of the respective system.

The GPS receiver system 316 is configured to receive signals from multiple satellites and to collect location specific relevant data and perform intelligent data analytics and computations to generate an output comprising a position and velocity solution according to various aspects of present disclosure. The communication system 318 is configured to establish communication between the user device 301 and external system(s)/device(s) through combination of one or more low power short range wireless communication channels up to 10 meters and long range RF communication methods up to 10 to 20 Km. In one embodiment, the communication system 318 comprises functionality and components that enable the device 301 to transmit and receive data according to one or more of communication standards such as, but not limited to, GSM, CDMA, GPRS, Wi-Fi, LAN, LORA and Bluetooth-LE. The display system 320 is configured to provide a visual output to the user of the device 301. The display system 320 comprises display devices such as, but not limited to, a display screen capable of displaying pictures, video and 3D pictures, 3D video, one or more LED status indicators, projectors, night vision lights, together with their associated drivers and ancillary components. The operating system 322 is configured to operate the device 301 in a more convenient way without any hassles. The operating system includes various preprogrammed instructions for performing various operations. It makes the device user-friendly and also to restore the device to initial position when required.

FIG. 3B is a block diagram illustrating plurality of sensors that may be used in the sensor system 304 of the smart wearable health monitoring device of the present disclosure. As shown there, the sensor system 304 comprises plurality of body/skin sensors used for monitoring various health parameters of an individual. The body/skin sensors comprise, but not limited to a temperature sensor 3041, a pressure sensor 3042, an oximeter 3043, a glucometer 3044, an ECG unit 3045, a fitness monitoring unit displaying number of calories burn, number of steps or distance traveled, and the like. It also comprises a blood alcohol and sweat analyzer to determine alcohol levels present in an individual. All the information obtained from each sensor (3041 through 3047) are processed and analyzed by using a central processing unit 314 to provide accurate health condition of the individual.

Figure 4:
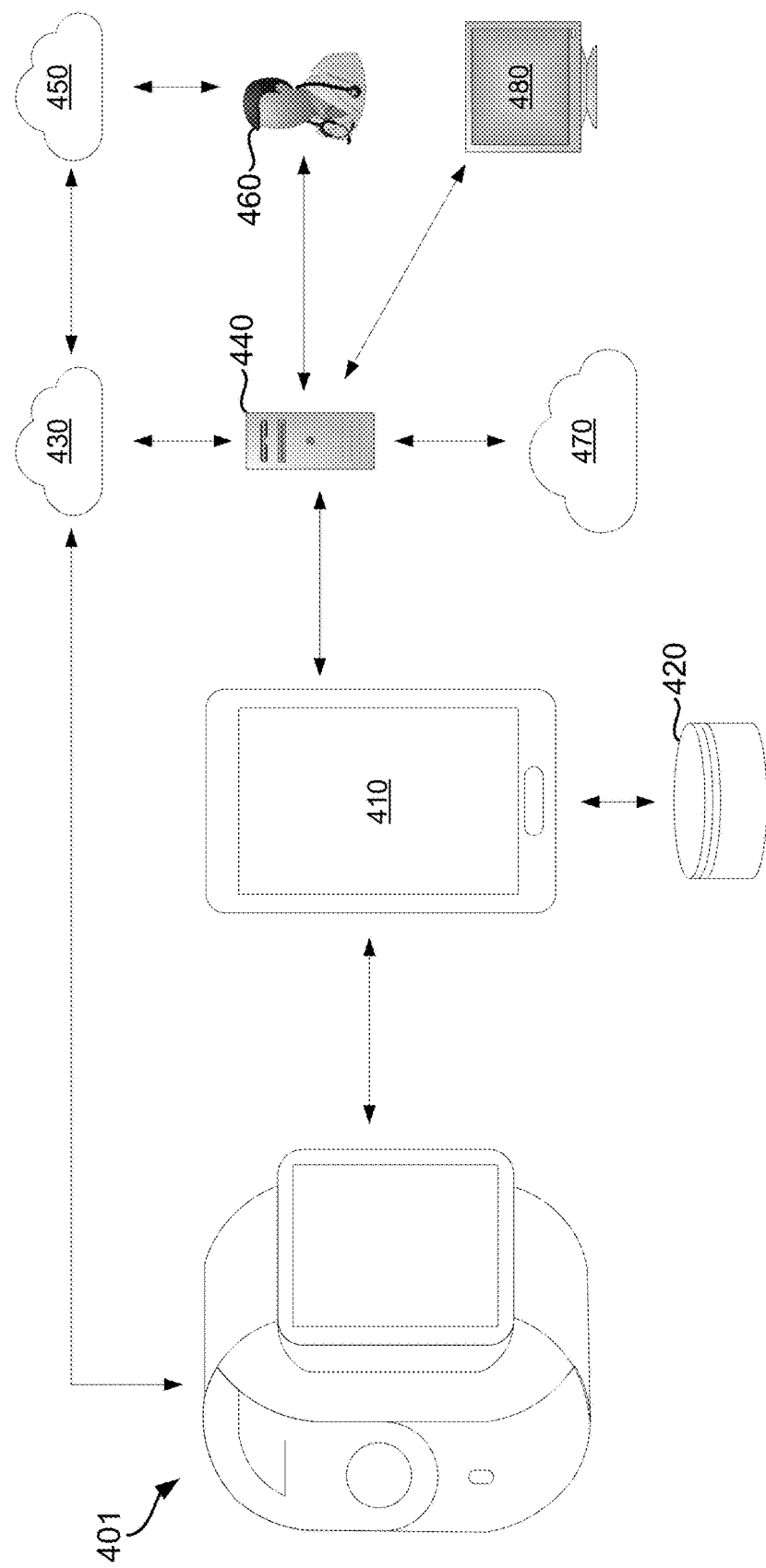
FIG. 4 is a block diagram illustrating an ecosystem comprising the smart wearable health monitoring device and various elements which helps in achieving medical assistance or medication delivery in another embodiment of the present disclosure.

FIG. 4 is a block diagram illustrating an ecosystem comprising the smart wearable health monitoring device and various elements which helps in achieving medical assistance or medication delivery in another embodiment of the present disclosure. The device 401 of the present disclosure collects and stores information related to health aspects of an individual regularly from various units of the device. In an embodiment, the stored information may be transferred to other devices or apparatus 410 using wireless communication channels. It is further provided that the data is stored with a secured user authentication provided as a pin or pattern or password to retain privacy of health reports of an individual. This data may be stored as local cache 420 in the other devices 410 but only accessible with user authentication.

In another embodiment, the daily reports on a regular basis may be uploaded into a web server 440 through secured wireless network channels 430 and synced with user profile stored in the web server 440. The web server 440 stores all the reports periodically along with date and time of the report generated corresponding to a user. The secured data from the device 401 may be sent directly to a trusted medical professional or advisor 460 through their medical facility secured wireless network channel 450. In an example, the user is able to upload the data from external devices 410 through wireless communication into the web server 440 for future access.

In yet another embodiment, the user may get access to his health reports directly from the web server 440 using a specially designed web portal 480 and also able to give permission or access to other individuals or medical personnel through the portal 480. Further, the user is also able to analyze his health status on his own by graphical comparison to his previous health reports. Further, the web server 440 provides tips and suggestions to the user through the web portal 480 for improved health benefits based on his health reports comparing to standards that are previously stored in the database. By using the web portal 480, the user is able to provide access to a specific medical advisor and gets his appointments and medication directions promptly without any delay. In an embodiment, a health analytic data platform 440 provides information related to a particular disease or majority of health concern in a particular area to various medical facilities in surrounding places. This helps in providing a best and prompt medication to the user of the device as well as to start new medical facilities in a particular area enabling business analytic models.

Figure 5:
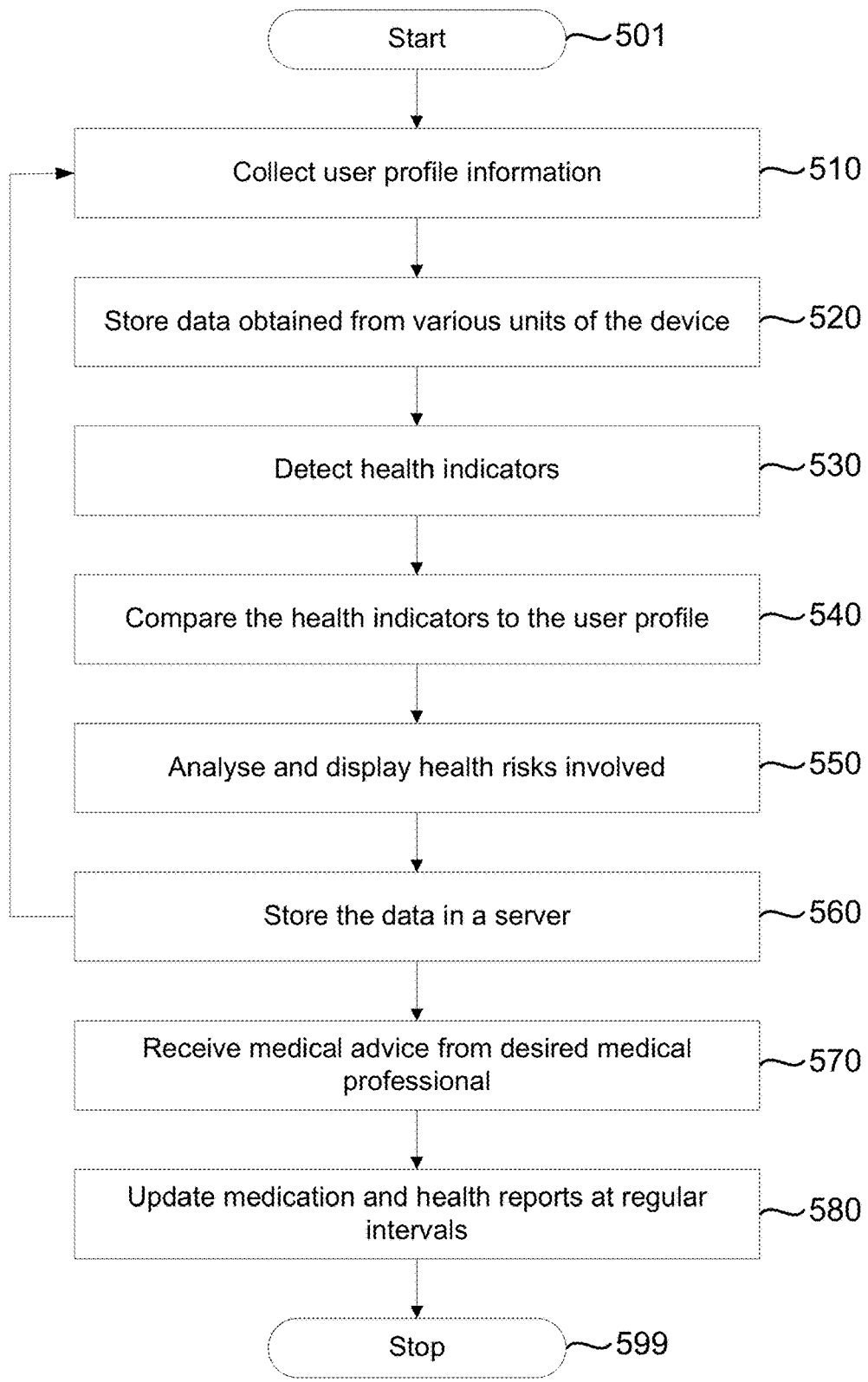
FIG. 5 is a flow chart illustrating the steps involved in monitoring health parameters of a patient in an embodiment of the present disclosure.

FIG. 5 is a flow chart illustrating the steps involved in monitoring health parameters of a patient in an embodiment of the present disclosure. The flowchart begins in step 501 and a control passes to the smart wearable device of the present disclosure. In step 510, the smart wearable device collects the user profile information comprising name, age, sex, height, weight, and other parameters. In an embodiment, these parameters are provided by the user to the device at start up.

In block 520, the device stores all the data obtained from plurality of units comprising blood pressure monitoring unit, blood glucose monitoring unit, ECG unit and from other body/skin sensors that are interconnected to the central processing unit. It further stores the information provided by the user in step 510. In block 530, health indicators are detected from the stored information obtained in step 520. The health indicators may comprise blood pressure, body temperature, blood glucose levels, ECG records and the like. These indicators are stored in the memory system of the device once recorded.

In block 540, the recorded health indicators are then compared to corresponding user profile and stored in a database. In an embodiment, the device may be used by multiple users in which the recorded health parameters may be assigned to a particular user manually by the user of the device in an account associated to the device. In block 550, the recorded health indicators with respect to a corresponding user are analyzed and determine risk involved by comparing to the standard health indicators as threshold limits provided within the device. In an embodiment, the standard health indicators may also comprise previous health reports or stats of the user to detect changes in his health conditions for early detection of diseases.

In block 560, the entire information comprising user profile, recorded health parameters corresponding to a specific user, and determined health risks are stored in a web server comprising a cloud database. This information is specific to a particular user and may be accessible only to the corresponding user or any other individual by providing user authentication. Further, this information is updated to the corresponding user profile information and is fed to step 510 where the updated user profile information along with previous health reports. In block 570, the health reports and the determined risks involved may thoroughly analyzed by a desired medical advisor or professional of the user choice in order to get a proper medication or advice to the user promptly.

In block 580, the medication or advice suggested by the medical advisor is stored into the database and updates along with the new health reports generated from the device of the present disclosure. This helps the user of the device to monitor his/her health conditions regularly without need to go medical facility by choosing a desired medical advisor of his/her own choice. The flowchart ends at 599. Further, the device of the present disclosure may be connected to the wireless communication channel by user interference in such a way that the user may switch on or off the wireless communication of the device as desired in order to reduce radio signals surrounding the user all the time.

Thus, the smart wearable health monitoring device of the present disclosure helps in providing a reliable and effective way to monitor various health parameters of an individual along with prompt and accurate medical assistance or medication delivery.

While various embodiments of the present disclosure have been described above, it should be understood that they have been presented by way of example only, and not limitation. Thus, the breadth and scope of the present disclosure should not be limited by any of the above-discussed embodiments, but should be defined only in accordance with the following claims and their equivalents.

What is claimed is:

1. A wearable device (201) comprising:
a central unit (202) similar to a wrist watch;
a flexible wristband (204) attached to the central unit (202) wherein the central unit and the flexible wristband together forming the wearable device for wearing on a wrist;
a first, a second and a third sensor pads (208A, 208B and 208C) mounted on the flexible wristband (204) wherein the first and the second sensor pads (208A and 208B) are mounted on the inner side of the flexible wristband (204) configured to touch a skin part on the wrist to collect a first and a second electrical signals from the respective locations when the wearable device (201) is tied around the wrist and the third sensor pad (208C) is mounted on outer surface of the flexible wrist-band (204) and configured to collect a third electrical signal when a finger is placed over the third sensor pad (208C);
an ejectable tray (1802) housed within the central unit (202);
a set of micro needle (170A) and enzyme test strip pairs (170B) housed in the ejectable tray (1802);
a fourth sensor pad (210) mounted on the outer surface of the flexible wrist-band (204) closer than the first and second sensor pads to the third sensor pad (208C) wherein the fourth sensor pad (210) operative as Photoplethysmogram (PPG) sensor providing a fourth electrical signal;
a spring and latch mechanism (1801 through 1806) deployed within the central unit (202) comprising a first spring (1805 or 1806) and a latch (1803 or 1804) to hold the ejectable tray (1802) within the central unit (202) and a second spring (1801), when activated, releases the latch (1803 and 1804) causing the ejectable tray (1802) to protrude outside of the central unit (202) for accessing at least one micro needle (170A) and enzyme test strip pair (170B);
a processor (314) mounted within the central unit (202) to process the first, the second, the third and the fourth electrical signals respectively received from the first, second, third, fourth sensor pads (208A, 208B, 208C and 210) and a fifth electrical signal from the enzyme test strip (170B), where-in the first, second, third, fourth sensor pads (208A, 208B, 208C and 210) and the enzyme test strip (170B) electrically coupled to the processor (314); and
a display device (320) integrated within the central unit (202) to display a plurality of health parameters determined from the first, the second, the third, the fourth and the fifth electrical signals.

2. The wearable device of claim 1, wherein the processor (314) generates an electrocardiogram from the first, the second and the third electrical signal and determines a blood glucose level from the fifth electrical signal.

3. The wearable device of claim 2, wherein the processor (314) determines a blood pressure from the first, the second, the third, and the fourth electrical signal.

4. The wearable device of claim 3, wherein the processor (314) determines the time difference between a first peak in the electrocardiogram determined by capturing signals from the first, second and third sensor pads (208A through 208C) and a corresponding peak in the Photoplethysmogram captured by the fourth sensor pad (210).

5. The wearable device of claim 4, wherein the processor (314) selectively displays, a heart rate determined from the electrocardiogram, a blood oxygen level determined from the Photoplethysmogram, the blood glucose level, the blood pressure, on the display device.

6. The wearable device of claim 5, further comprising a USB interface connector attached to the flexible wristband and electrically coupled to the processor for external interface such that the USB connector operates as a buckle to the wristband.

7. The wearable device of claim 5, wherein the central unit (202) further comprises a memory (310) configured to store the health parameters including the heart rate, the electrocardiogram, the blood oxygen level, the Photoplethysmogram, the blood glucose level and the blood pressure.

8. The wearable device of claim 5, wherein the central unit (202) further comprises a first button to activate the second spring, a second button to select the health parameter for display, and a third button to configure the central unit.

9. The wearable device of claim 5, wherein the central unit (202) further comprises a wireless communication transceiver to transfer the data stored in the memory (310) to a desired destination device.

10. The wearable device of claim 3, further comprising an inflatable inner flap coupled to a micro pump and a solenoid facilitating inflation and deflation of the inner flap for measuring blood pressure.

* * * * *